United States Patent [19]
Moise et al.

[11] Patent Number: 4,895,557
[45] Date of Patent: Jan. 23, 1990

[54] DRIVE MECHANISM FOR POWERING INTRAVASCULAR BLOOD PUMPS

[75] Inventors: John C. Moise, Carmichael; John W. Carriker, Gold River, both of Calif.; Reginald R. Baxter, Barrington, Ill.

[73] Assignee: Nimbus Medical, Inc., Rancho Cordova, Calif.

[21] Appl. No.: 129,714

[22] Filed: Dec. 7, 1987

[51] Int. Cl.$^4$ .............................................. A61F 1/24
[52] U.S. Cl. ..................................... 600/16; 604/151; 623/3; 415/900
[58] Field of Search ................ 128/1 D, 305, DIG. 3; 604/22, 151, 267; 623/3; 415/DIG. 4, 213 C; 417/352–354; 310/54; 600/16–18

[56] References Cited

U.S. PATENT DOCUMENTS

| | | | |
|---|---|---|---|
| 3,568,659 | 3/1971 | Karnegis | 128/1 D |
| 3,904,901 | 9/1975 | Renard et al. | 310/54 |
| 4,102,610 | 7/1978 | Taboada et al. | 128/1 D |
| 4,445,509 | 5/1984 | Auth | 604/266 |
| 4,591,355 | 5/1986 | Hilse | 128/305 |
| 4,625,712 | 12/1986 | Wampler | 128/1 D |
| 4,631,052 | 12/1986 | Kensey | 604/22 |
| 4,688,998 | 8/1987 | Olsen et al. | 128/1 D |
| 4,729,763 | 3/1988 | Henrie | 604/22 |
| 4,753,221 | 6/1988 | Kensey et al. | 128/1 D |

Primary Examiner—Stephen C. Pellegrino
Assistant Examiner—Ralph Lewis
Attorney, Agent, or Firm—Weissenberger & Peterson

[57] ABSTRACT

A disposable, sterilizable cable drive unit for an intravascular blood pump includes a rotor enclosed in a fluid-tight enclosure which can be slipped into the stator of a drive motor. The unit is connectable to a constant-rate purge fluid supply and to a dual-lumen cable sheath. One lumen provides a sterile purge fluid path; the other carries the drive cable to the blood pump and provides a return path for a flushing fluid in which the cable is immersed. The flushing unit is derived from the purge fluid supply at a constant rate, and the rotor may also be immersed in it if desired. The unit is held in the drive motor by a manually operated detent, and the self-centering action of the rotor aligns it with the stator when the motor is energized. The motor is mounted on a gimbal so as to be alignable with the cable sheath at its point of insertion into the patient's vascular system, in order to prevent stresses on the patient and kinks in the cable sheath.

15 Claims, 4 Drawing Sheets

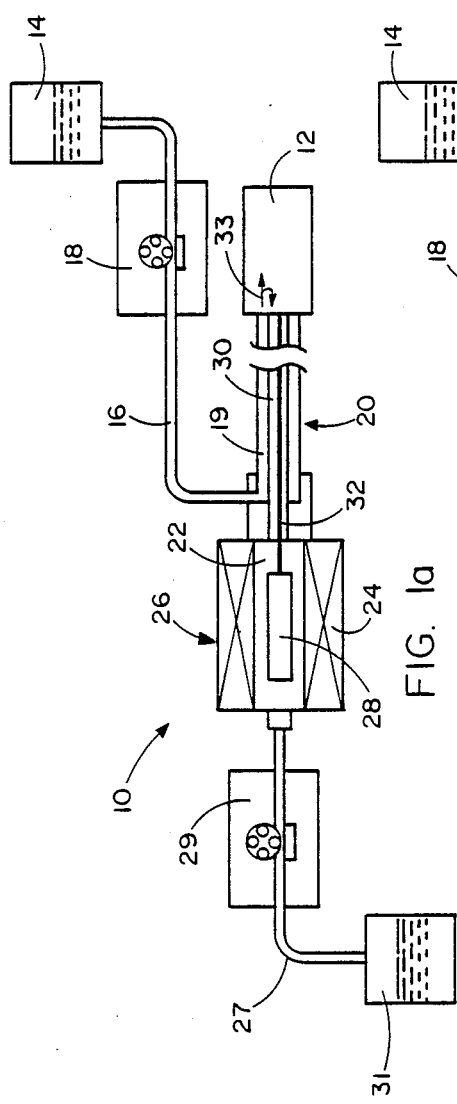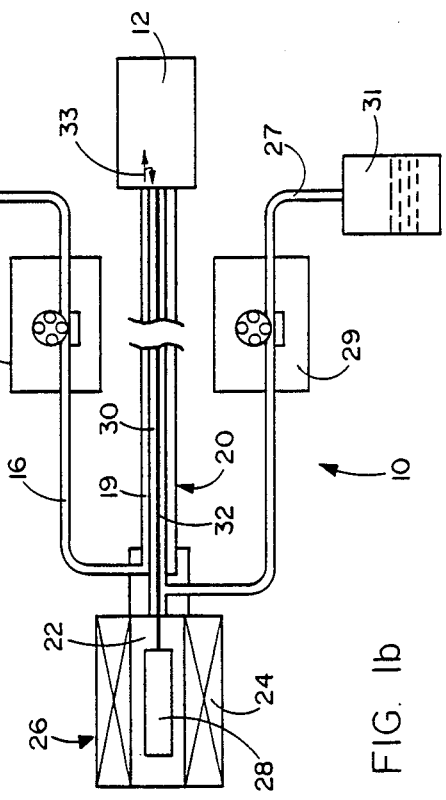
FIG. 1a
FIG. 1b

DRIVE MECHANISM FOR POWERING INTRAVASCULAR BLOOD PUMPS

FIELD OF THE INVENTION

This invention relates to an extracorporeal drive mechanism and purge fluid supply for an intravascular blood pump particularly adapted to facilitate threading the blood pump through a blood vessel, and to allow disposal of the entire rotary portion of the drive.

BACKGROUND OF THE INVENTION

U.S. Pat. No. 4,625,712 and copending application Ser. No. 129,713 filed Dec. 7, 1987 disclose miniature high-speed blood pumps which can be threaded through a blood vessel to provide rapid heart assist without major surgery. These blood pumps are driven from outside the body by a flexible cable encased in a cable sheath attached to the pump. The cable is powered by an electric motor, and the cable sheath also serves as the purge fluid supply to the hydrostatic purge seal and bearings of the pump.

Three specific problems are produced by this environment: for one, the entire purge fluid path and cable must be sterilizable and disposable; secondly, any debris produced by the abrasion of the sheath by the cable must not be permitted to enter the pump; and thirdly, the motor must be firmly positionable on the patient so as to cause the least possible discomfort, and to keep the cable as steady and straight as possible, after the blood pump and cable sheath have been threaded through the vascular system.

SUMMARY OF THE INVENTION

The present invention solves the above-stated problems by (1) placing the rotor of the cable drive motor in a fluid-tight, sterilizable enclosure which can be slipped into the stator of the motor, and pulled out and disposed of after use, and (2) gimbaling the motor so that it can be aligned with the cable sheath proximally to the point of percutaneous insertion.

More specifically, in the device of the invention, purge fluid from a sterile container such as an IV bag is pumped at a constant flow rate (to maintain a substantially constant purge flow in the blood pump in spite of variability in the operating characteristic of the pump) by an appropriate roller or peristaltic pump through sterile IV tubing. The IV tubing is connected to one lumen of a dual-lumen cable sheath. The cable sheath is attached to a fluid-tight cable drive unit which can be removably inserted into the stator of a gimbaled cable drive motor. The cable drive unit contains the rotor of the cable drive motor, and may also serve as a flushing fluid passage from the other lumen of the cable sheath to a disposal container through the cable drive motor. The flushing fluid (which is derived from the purge fluid at its entrance into the blood pump) is also conveyed to the disposal container through a roller or peristaltic pump so as to maintain a constant net purge flow through the blood pump.

The cable sheath, which is connected at one end to the blood pump and at the other end to the cable drive unit, can be packaged and sterilized together with the blood pump and cable drive unit. The cable sheath provides a sheath for the drive cable, and also serves as a purge fluid conduit to the blood pump as well as a return conduit for the flushing fluid in which the drive cable is immersed.

When the blood pump has been fully inserted through, e.g., the femoral artery, the gimbaled cable drive motor is strapped to the patient's leg adjacent the percutaneous insertion point and is aligned with the cable sheath so as to prevent stresses at the insertion point.

It is thus one object of the invention to provide a motor for a cable-driven blood pump in which the cable sheath, cable, rotor and blood pump are parts of a single, disposble sterilizable unit.

It is a further object of the invention to provide in connection with that unit a means for drawing a predetermined quantity of flushing fluid from the purge fluid stream in the unit and using it to flush abraded debris in the cable sheath away from the blood pump.

It is another object of the invention to provide a motor for a cable-driven intravascular blood pump which is gimbaled so as to be alignable with the cable sheath when strapped to the patient's leg.

BRIEF DESCRIPTION OF THE DRAWINGS

FIG. 1a is a schematic diagram illustrating the components of the inventive system in one preferred embodiment of the invention;

FIG. 1b is a schematic diagram illustrating the same components in another preferred embodiment of the invention;

FIG. 3 is an overall axial section of the disposable cable drive unit of FIG. 1a.

DESCRIPTION OF THE PREFERRED EMBODIMENT

Figure 2:
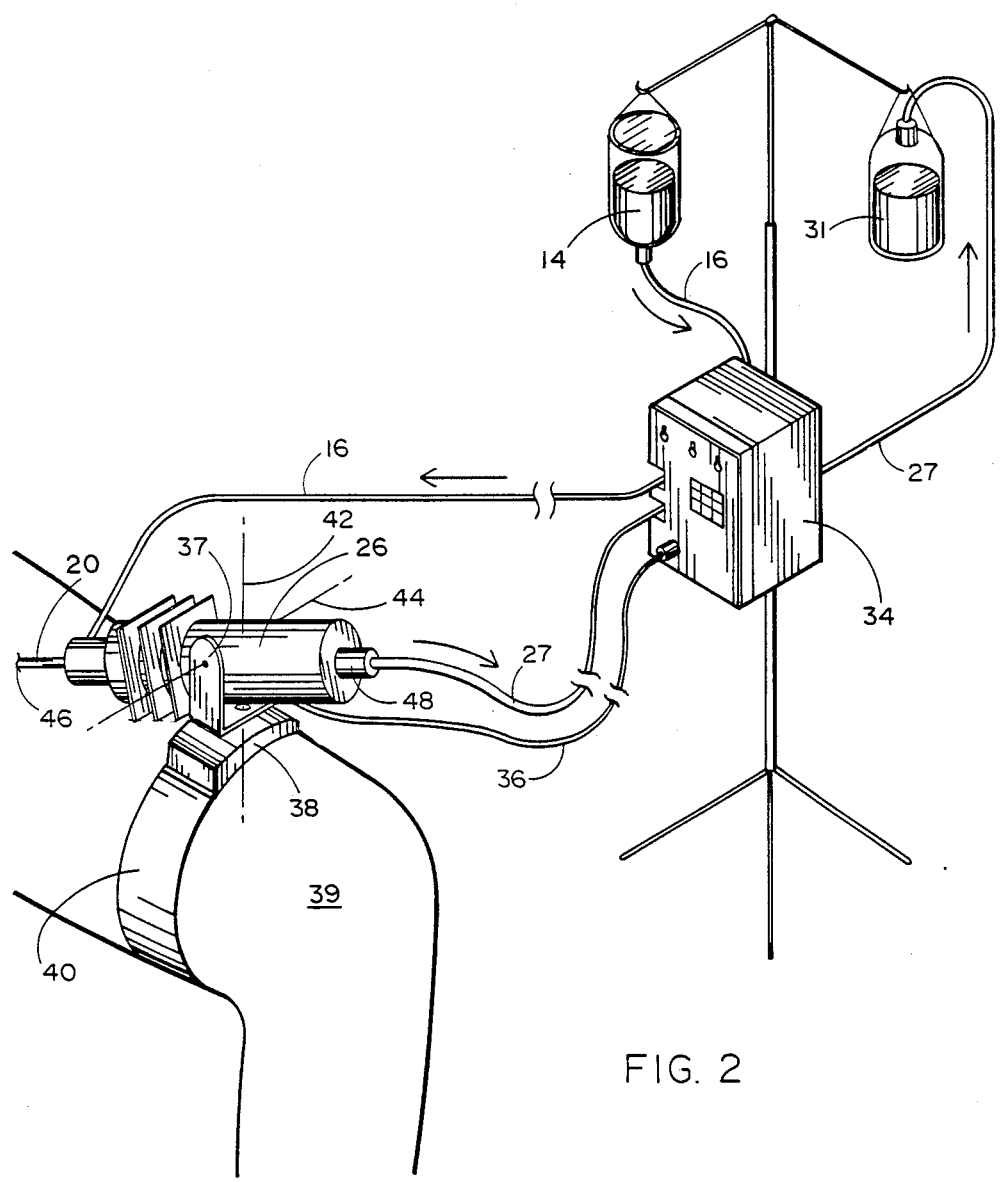
FIG. 2 is a perspective view of the gimbaled cable drive motor in a patient environment.

FIG. 1a shows in diagrammatic form the system 10 of this invention. A blood-compatible purge fluid for the hydrodynamic and hydrostatic bearings of an intravascular blood pump 12 is stored in a sterile container such as an IV bag 14.

Sterile IV tubing 16 is clamped into an appropriate roller or peristaltic pump 18 which pumps purge fluid through the tubing 16 at a constant rate. This is necessary in order to maintain a constant purge fluid flow through the hydrostatic purge-sealed bearing of the blood pump 12 in spite of variations in the operating characteristics of the pump 12. Blood pumps of this type are disclosed in U.S. Pat. No. 4,625,712 and in the above-mentioned copending application Serial No.

The downstream end of IV tubing 16 is connected to the outer lumen 19 of a cable sheath 20 which connects the cable drive unit 22 (the cable drive unit 22 being inserted into the stator 24 of a cable drive motor 26) to the blood pump 12. The cable drive unit 22 contains the rotor 28 of motor 26. In the embodiment of FIG. 1a, the cable drive unit 22 also functions as a fluid passage for conveying flushing fluid from the inner lumen 30 of the cable sheath 20 through tubing 27 and a roller of peristaltic pump 29 to a disposal container 31. The outer lumen of cable sheath 20 serves as a purge fluid passage, while the inner lumen 30 serves as a sheath for the drive cable 32 which is attached to the rotor 28 and which powers the blood pump 12. The drive cable 32 is immersed in the flushing fluid which is derived from the purge fluid supply in the pump 12, as schematically indicated by arrow 33. The details of the structure accomplishing this result are shown in copending application Ser. No. 129,173. The purpose of this arrangement is to prevent any debris which may be abraded from the cable sheath wall by the drive cable 32 from entering the pump 12.

In the embodiment of FIG. 1a, the flushing fluid is drawn through the cable drive unit 22 where it assists in lubricating and cooling the rotor 28. In the alternative embodiment of FIG. 1b, the flushing fluid is drawn off from the lumen 30 before reaching the rotor 28. In all other respects, the embodiments of FIGS. 1a and 1b are the same.

The roller pump 29 is provided so as to precisely regulate the flow of flushing fluid, so that an exactly predetermined portion of the purge fluid pumped by roller pump 18 will be drawn off as flushing fluid, leaving an equally precise amount of purge fluid for purging the purge-sealed bearing of blood pump 12.

The general environment in which the system 10 may be used is illustrated in FIG. 2. FIG. 2 schematically shows a control console 34 which may contain the roller pumps 18 and 29 of FIGS. 1a and 1b as well as controls for the motor 26. The motor is controlled from console 34 via a cable 36. The motor 26 is supported on a gimbal 37 which is preferably mounted on a curved plate 38 attached to the patient's leg 39 by a strap 40. This allows motor 26 to be freely moved about orthogonal axes 42, 44. The motor 26 can thus be aligned with the cable sheath 20 at its point of insertion 46 into the femoral artery of the patient. The free movement of motor 26 is important in this environment, as stresses at the insertion point 46 and bends in the delicate cable sheath must be avoided where possible in order to prevent discomfort to the patient and to minimize any abrasion of the inner lumen wall by the drive cable 36.

Figure 3:
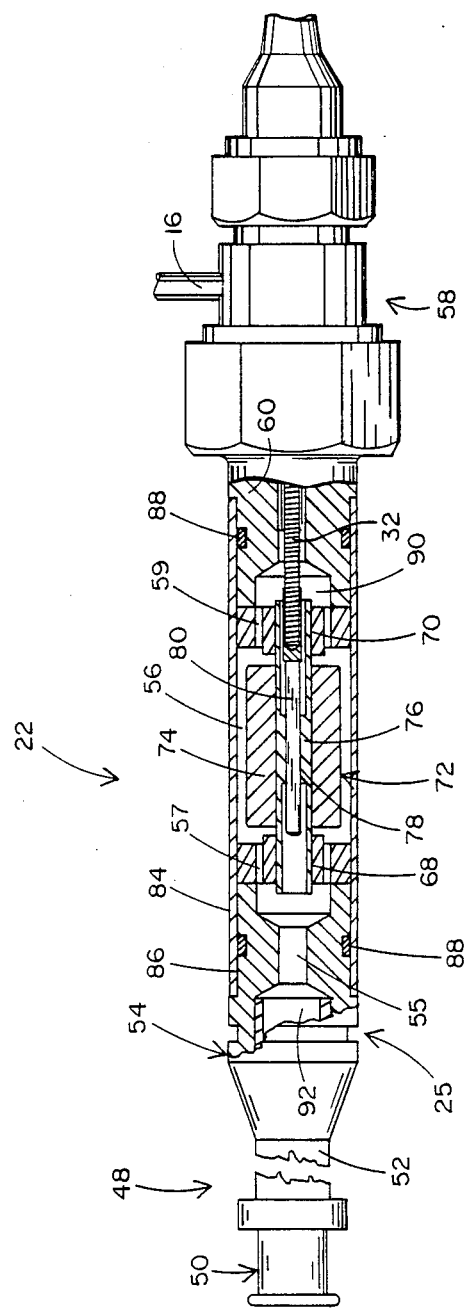

FIG. 3 shows the disposable cable drive unit 22 of this invention in greater detail. The tube connector assembly 48 includes a tube fitting 50 to which the IV tubing 16 can be attached. A rigid tube 52 connects the fitting 50 to a tube connector block 54 which has fluid passages 55, 57 and 59 and a fluid chamber 56 therein. Tube connector assembly 48 also has a groove 25 to engage a manually operated spring detent (not shown) in the motor 26 for a positive retention of the cable drive unit in the motor 26 during use.

On the other end of the cable unit 22, the cable sheath 20 is connected to the cable drive unit 22 by a connector assembly 58 forming part of cable drive unit 22 and including a connector block 60 (which is shown in more detail in FIG. 4) as described below.

The connector blocks 54, 60 enclose between them a pair of hydrodynamic bearings 68, 70 in which the rotor assembly 72 is rotatably mounted. The rotor assembly 72 includes a rotor 74 which may be formed of a neodymium-boron-iron alloy coated with plastic to protect the corrosion-prone rotor 74 from the purge fluid in which it operates. The magnetic nature of rotor 74 makes it axially self-aligning with the motor stator 24.

The rotor 74 is mounted on a shaft 76 which has a non-circular drive hole 78 at its midsection. The drive hole 78 receives a spline 80 to which the flexible cable 32 is attached. This allows limited free axial movement of the cable 32 with respect to the cable drive unit 22 in order to accommodate the bending of the cable sheath 20 in use.

The rotor assembly 72 is encased in a sleeve 84 which is bonded to the connector blocks 54, 60 at 86 and forms a fluid-tight seal with them by means of O-rings 88. In the embodiment of FIG. 1a, fluid flows through the cable drive unit 22 from chamber 90 through passages 59 into chamber 56; and then through passages 57 into passage 55 and 92. From there, it flows through tubing 27 into the disposal container 31.

Figure 4:
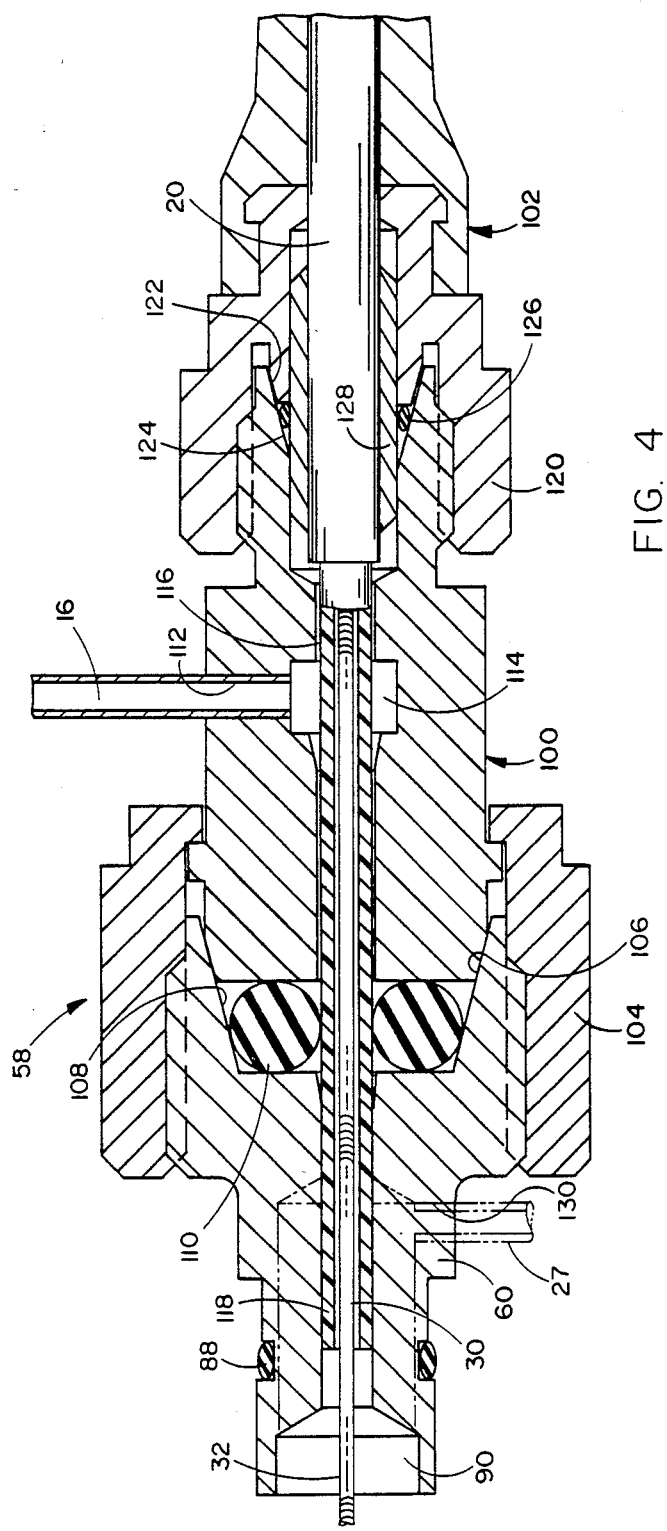
FIG. 4 is a detail axial section of a portion of the cable drive unit of FIG. 3.

Turning now to FIG. 4, the connector assembly 58 includes the connector block 60, an adapter 100, and an elastomeric strain relief fitting 102. The adapter 100 is secured to the connector block 60 by a screwthreaded collar 104. The adaptor 100 has a tapered surface 106 which coacts with surface 108 of connector block 60 to limit the insertion of adapter 100 into connector block 60. When fully inserted, the adapter compresses O-ring 110 sufficiently to form a fluid-tight connection with connector block 60 and the wall 118 of the inner lumen 30.

The adapter 100 includes an opening 112 which receives the tubing 16 of FIG. 1. The opening 112 communicates with a plenum 114 which in turn communicates with the outer lumen 19 of the cable sheath 20 through passage 116. The wall 118 of the inner lumen 30 is extended through adapter 100 into the connector block 60, so that it communicates with chamber 90.

The cable sheath 20 is held in the strain relief fitting 102, which can be screwthreadedly secured to the adapter 100 by collar 120. The fitting 120 also has a tapered surface 122 which, together with the surface 124 of adapter 100, limits the insertion of fitting 102 into adapter 100. When fully inserted, the fitting 102 compresses O-ring 126 sufficiently to form a fluid-tight seal between collar 120 and adapter 100, as well as between adapter 100 and the reinforcement sleeve 128 which is bonded to the end of cable sheath 20.

It will be understood that although FIGS. 3 and 4 reflect the embodiment of FIG. 1a, the cable drive unit 22 can be readily adapted to the embodiment of FIG. 1b, as shown in phantom lines in FIG. 4, by adding to the connector block 60 a second opening 130 communicating with the passage 90 and with the tubing 27 of FIG. 1b, and by sealing the outer end of tube connector block 54. Alternatively, the tubing 27 may be connected to the inner lumen 30 of cable sheath 30 through an appropriate passage in adapter 100 (not shown).

It will be seen that the present invention provides a cable drive for an intravascular blood pump which is sterilizable and disposable as a unit together with the cable sheath and blood pump itself. The cable drive unit is easily inserted into the stator of a drive motor, and the motor is gimbaled to allow it to be aligned with the percutaneous insertion point, when strapped to a patient's leg, for the prevention of stresses and kinks.

We claim:

1. A cable drive for an intravascular blood pump, comprising:
   (a) a motor having a stator surrounding a hollow space; and
   (b) a cable drive unit removably insertable into said hollow space, said cable drive unit including:
      (i) fluid-tight housing means having a fluid inlet and a fluid outlet, and a fluid passage connecting the same;
      (ii) rotor means disposed within said housing means, said rotor means being arranged to be rotated when said housing means is inserted into said stator and said stator is energized; and (iii) means on said rotor means for receiving a drive cable extending though said fluid outlet.

2. A combined sterilizable drive and purge fluid supply system for an intravascular blood pump, comprising:
(a) a source of purge fluid;
(b) an intravascular blood pump;
(c) cable sheath means connected to said blood pump for conveying purge fluid to said blood pump;
(d) flexible cable means connected to said blood pump for driving said blood pump, said cable means being positioned in said cable sheath means longitudinally thereof;
(e) a drive motor stator surrounding a hollow space;
(f) a fluid-tight cable drive removably insertable into said hollow space said cable drive unit including
 (i) a housing; and
 (ii) rotor means rotatably supported within said housing, said rotor means being connected to said cable means to rotate the same;
(g) tubing means for conveying said purge fluid from said purge fluid source to said cable drive unit; and
(h) purge fluid pump means for pumping purge fluid through said tubing means, said tubing means, cable drive unit and cable sheath being interconnected so as to provide a continuous purge fluid flow path therethrough from said purge fluid source to said blood pump.

3. The system of claim 2, in which said cable sheath means include a pair of lumens, one of said lumens being conectable to said tubing means, and the other lumen containing said cable means and being connectable to fluid discharge means.

4. The system of claim 3, further comprising discharge pump means for pumping fluid through said other lumen toward said fluid discharge means.

5. The system of claim 4, in which said discharge pump means are of a type arranged to convey fluid at a constant rate toward said fluid discharge means.

6. The system of claim 3, in which said cable drive unit further includes a fluid passage through said housing, and said other lumen is connectable to said fluid discharge means through said fluid passage.

7. The system of claim 6, in which said rotor is positioned in said fluid passage.

8. The system of claim 7, in which said rotor is coated to prevent corrosion by the fluid in said fluid passage.

9. The system of claim 2, in which said stator is gimbaled so that its axis is substantially omnidirectionally movable.

10. The system of claim 2, in which the interconnection between said rotor means and said cable means is such as to permit free relative movement between said rotor means and said cable means in the axial direction but not in the rotary direction.

11. The system of claim 2, in which said purge fluid pump means are of a type arranged to convey fluid at a constant rate through said tubing.

12. A disposable, sterilizable intravascular axial flow blood pump assembly, comprising:
(a) a blood pump;
(b) a cable drive unit insertable into and removable from a hollow space formed by the stator of an elector motor without disassembly of said motor said cable drive unit including a rotor for said motor;
(c) a cable sheath connecting said blood pump and said cable drive unit in fluid tight relationship; and
(d) a flexible drive cable operatively connecting said motor rotor and the rotor of said blood pump;
(e) said drive cable extending through said cable sheath, and said cable sheath forming a fluid conduit for conveying fluid between said cable drive unit and said blood pump.

13. A disposable, sterilizable intravascular axial flow blood pump assembly, comprising:
(a) a blood pump;
(b) a cable drive unit removable insertable into a hollow space formed by the stator of an electric motor, said cable drive unit including a rotor for said motor;
(c) a cable sheath connecting said blood pump and said cable drive unit in fluid tight relationship; and
(d) a flexible drive cable operatively connecting said motor rotor and the rotor of said blood pump;
(e) said drive cable extending through said cable sheath, and said cable sheath forming a fluid conduit for conveying fluid between said cable drive unit and said blood pump; and
(f) said cable sheath having a pair of lumens, one of said lumens forming a fluid path for conveying purge fluid from said cable drive unit to said blood pump, the other of said lumens forming a fluid path for conveying flushing fluid from said blood pump to said cable drive unit, and said drive cable extending through said other lumen.

14. The assembly of claim 13, in which said lumens are substantially concentric.

15. The assembly of claim 13, further including means for diverting a portion of any fluid flowing through said one lumen toward said blood pump into said other lumen at said blood pump for returning it to said cable drive unit.

* * * * *